United States Patent
Deshpande et al.

(10) Patent No.: US 6,936,711 B2
(45) Date of Patent: Aug. 30, 2005

(54) PROCESS FOR PREPARATION OF PENAM DERIVATIVES FROM CEPHAM DERIVATIVES

(75) Inventors: Pandurang Balwant Deshpande, Chennai (IN); Senthil Kumar Udayampalayam Palanisamy, Tamilnadu (IN); Gnanaprakasam Andrew, Chennai (IN)

(73) Assignee: Orchid Chemicals and Pharmaceuticals Limited, Tamilnadu, IN (US)

( * ) Notice: Subject to any disclaimer, the term of this patent is extended or adjusted under 35 U.S.C. 154(b) by 280 days.

(21) Appl. No.: 10/309,201

(22) Filed: Dec. 4, 2002

(65) Prior Publication Data

US 2003/0232983 A1 Dec. 18, 2003

(30) Foreign Application Priority Data

Jun. 7, 2002 (IN) ................................. 434/MAS/2002
Jun. 12, 2002 (WO) ............................... PCT/IB02/02230

(51) Int. Cl.⁷ .......................................... C07D 499/06
(52) U.S. Cl. ..................................................... 540/310
(58) Field of Search ........................................ 540/310

(56) References Cited

U.S. PATENT DOCUMENTS

| | | |
|---|---|---|
| 4,529,592 A | 7/1985 | Micetich et al. |
| 4,562,073 A | 12/1985 | Micetich et al. |
| 4,585,874 A * | 4/1986 | Alpegiani et al. .......... 540/310 |
| 4,668,514 A | 5/1987 | Micetich et al. |
| 4,895,941 A | 1/1990 | Torii et al. |

FOREIGN PATENT DOCUMENTS

| | | |
|---|---|---|
| EP | 0 097 446 A1 | 1/1984 |
| EP | 0 273 699 A2 | 7/1988 |
| EP | 0 306 924 A1 | 3/1989 |

* cited by examiner

Primary Examiner—Mark L. Berch
(74) Attorney, Agent, or Firm—Oliff & Berridge, PLC

(57) ABSTRACT

The present invention relates to a process for preparing 2α-methyl-2β-substituted methyl penam derivatives from cepham derivatives, more particularly the present invention provides a novel process for preparing 2β-heterocyclyl methyl penam derivatives of the formula (I)

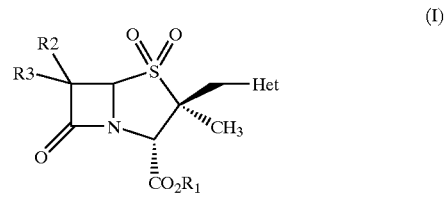

by reacting a cepham compound with a heterocylic amine to form an intermediate compound, and oxidizing the intermediate compound to produce the 2β-heterocyclyl methyl penam derivatives of the formula (I), wherein $R_1$ represents carboxylic acid protecting group; $R_2$ and $R_3$ may be same or different and independently represent hydrogen, halogen, $NH_2$, acylamino, phthalimido with a proviso that both $R_2$ and $R_3$ are not $NH_2$, acylamino, phthalimido; Het represents a 5 or 6 membered nitrogen containing heterocycle ring system having one or more heteroatoms selected from O, S, or N.

20 Claims, No Drawings

PROCESS FOR PREPARATION OF PENAM DERIVATIVES FROM CEPHAM DERIVATIVES

FIELD OF THE INVENTION

The present invention relates to a process for preparing 2α-methyl-2β-substituted methyl penam derivatives from cepham derivatives. More particularly, the present invention provides a novel process for preparing 2β-heterocyclyl methyl penam derivatives of the formula (I)

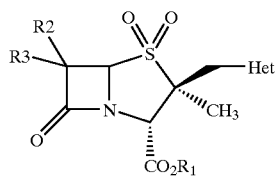
(I)

wherein $R_1$ represents carboxylic acid protecting group; $R_2$ and $R_3$ may be same or different and independently represent hydrogen, halogen, $NH_2$, acylamino, phthalimido with a proviso that both $R_2$ and $R_3$ are not $NH_2$, acylamino, phthalimido; Het represents a 5 or 6 membered nitrogen containing heterocycle ring system having one or more heteroatoms selected from O, S, or N.

The 2β-heterocyclyl methyl penam derivatives of the formula (I) are useful for the preparation of tazobactam, its derivatives or its salts of formula (X)

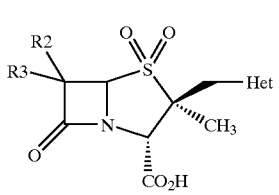
(X)

wherein $R_2$ and $R_3$ may be same or different and independently represent hydrogen, halogen, $NH_2$, acylamino, phthalimido with a proviso that both $R_2$ and $R_3$ are not $NH_2$, acylamino, phthalimido; Het represents a 5 or 6 membered nitrogen containing heterocycle ring system having one or more heteroatoms.

The utility of β-lactam antibiotics is limited by the resistance exhibited by the microorganisms, through the action of β-lactamase enzyme. The enzyme acts through cleavage of β-lactam ring of these antibiotics, thereby destroying the drug leading to loss of activity. Therefore, it requires β-lactamase inhibitors, which can counteract with the β-lactamase enzyme and eliminate the drug resistance. The β-lactamase inhibitors are used along with β-lactam antibiotics to promote the antibiotic activity. Thus research on new β-lactamase inhibitors and novel processes for their production is continuing.

BACKGROUND OF THE INVENTION

Several patents have disclosed various methods of producing 2β-substituted methyl penam derivative. For instance, U.S. Pat. Nos. 4,529,592, 4,562,073, & 4,668,514 and EP 97446 discloses a process, which involves treatment of 2β-azidomethyl penam derivatives of the formula (II):

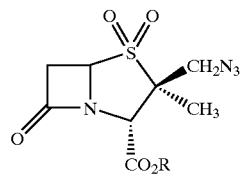
(II)

wherein R represents a carboxy-protecting group, with acetylene/acetylene derivative or vinyl derivative under high pressure in a sealed reactor and at elevated temperatures followed by deprotection with a suitable reagent to get the β-lactamase inhibitor of the formula (I).

The 2β-azidomethyl penam derivative of the formula (II) was in turn prepared from the 2β-substituted methyl penam derivatives of the formula (III)

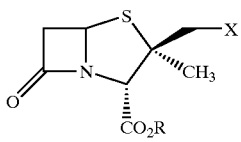
(III)

wherein R represents carboxy-protecting group; X represents chloro or bromo, by treating with sodium azide in aqueous polar aprotic solvents, followed by oxidation.

The above method suffers from the limitation of introducing only very few heterocycles like 1,2,3-triazole group, but not a wide variety of other heterocycles. In addition, the method requires handling of acetylene gas at high pressure and high temperature, which carries inherent hazard owing to its high detonation velocity, thus rendering it non industrial and eco-friendly. Added to it, this process also requires handling of excess sodium azide, leaving behind large quantities of azide for ETP treatment which is hazardous owing to the release of hydrazoic acid as it is a potential explosive and a serious health hazard.

The EP 0273699 discloses a different approach, which involves the preparation of 2β-triazolylmethylpenam derivatives of the formula (IV)

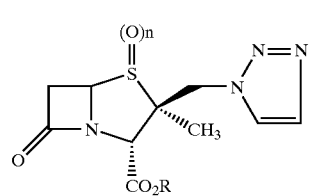
(IV)

wherein R represents carboxy protecting group, n=0, by the treatment of 2β-halomethyl penam derivative of the formula (III)

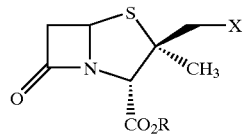
(III)

wherein X represents chlorine or bromine; R represents carboxy-protecting group, with 1H-1,2,3-triazole. The product obtained can be oxidized and deprotected to get the 2β-substituted methyl penam derivatives of the formula (I).

EP 306924 discloses a reduction method employing lead compounds like lead chloride or lead bromide to prepare 2β-triazolylmethyl penam derivative of the formula (IV) (n=0–2) from 6,6-dibromo-2β-triazolylmethyl penam derivative of the formula (V).

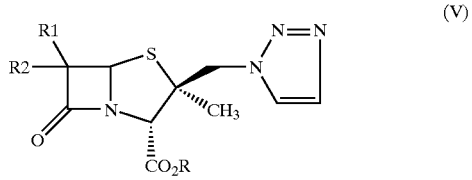

wherein $R^1$, and $R^2$ may be same or different and represent H or bromine; R is a carboxy-protecting group.

In yet another method disclosed in the U.S. Pat. No. 4,895,941, the penam sulfoxide of the formula (VI)

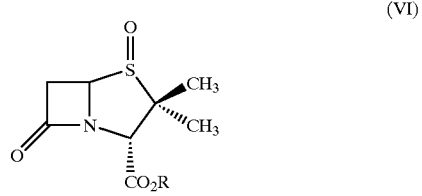

wherein R represents carboxy-protecting group, is treated with 2-trimethylsilyl-1,2,3-triazole in a sealed tube at elevated temperatures to give a mixture, which requires purification by column chromatography to isolate the 2β-triazolylmethyl penam derivative of the formula (IV) (n=0).

In most of the methods involved, 2β-halomethylpenam of the formula (III) is used as the key intermediate. This is true with both the azide route and the triazole route discussed above. However, the five-membered 2-halomethyl penam of the formula (III) itself is an unstable intermediate and therefore manufacturing of this intermediate in large quantities and storing is always cumbersome. This intermediate has been found to degrade on storage even at low temperatures in isolated form as well in the solvent from which it is isolated. Thus all the operations related to preparation of this intermediate have to be done rapidly and the isolated intermediate has to be converted to the final product immediately. As a result of these limitations, the scale up in plant always affords less yield and low quality, which ultimately leads to low level of consistency.

All the above described processes are associated with one or more of the following limitations: (i) unstable nature of the key intermediate (ii) use of hazardous and explosive reagents (iii) requirement of high pressures coupled with elevated temperatures—especially with acetylene (iv) use of large excess of sodium azide and its consequent environmental and explosion issues (v) use of highly toxic and polluting compounds of heavy metals like lead, especially in the penultimate stages of pharmaceuticals. These factors affect the consistency in quality and yield of the intermediates and the final product as well as safety on manufacturing scale.

To overcome the foregoing limitations, we were searching for a novel process, which involves stable intermediates and safe reagents/reaction conditions to manufacture 2β-substituted methyl penams. In our laboratory, we conducted extensive research and investigated a variety of synthetic schemes and methodologies to find a novel solution for manufacturing the said penam.

As a result of our continued efforts, we could identify a new route, which employs a cepham moiety unlike the penam derivatives employed so far. The advantage of the application of the six-membered cepham moiety is that it is a stable intermediate unlike the penams employed so far, and therefore utilization of this intermediate would reflect in overcoming the limitations discussed above.

While in all the available literature 2β-chloromethylpenams of the formula (III) were employed to prepare 2β-triazolylmethyl substituted penams of the formula (IV), whereas the present invention relies on ring-contraction phenomenon of converting the six-membered 3-halomethyl cephams of the formula (VII) in to 2β-heterocyclyl methyl penams of the formula (I).

OBJECTIVE OF INVENTION

The main objective of the present invention is to provide a process for the preparation of 2β-heterocyclyl methyl penam derivatives of the formula (I), which involves the conversion of six-membered cepham moiety.

Another objective of the present invention is to provide a process for the preparation of 2β-heterocyclyl methyl penam derivatives of the formula (I), in good yields and high purity.

Still another objective of the present invention is to provide a process for the preparation of 2β-heterocyclyl methyl penam derivatives of the formula (I), in pure form and not contaminated with the other isomers.

SUMMARY OF THE INVENTION

Accordingly, the present invention provides a process for the preparation of 2β-heterocyclyl methyl penam derivatives of the formula (I),

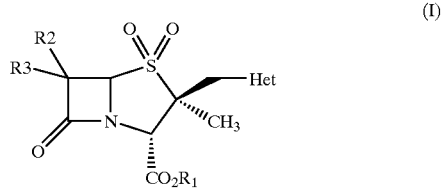

wherein $R_1$ represents carboxylic acid protecting group; $R_2$ and $R_3$ may be same or different and independently represent hydrogen, halogen, $NH_2$, acylamino, phthalimido with a proviso that both $R_2$ and $R_3$ are not $NH_2$, acylamino, phthalimido; Het represents a 5 or 6 membered nitrogen containing heterocycle ring system having one or more heteroatoms selected from O, S, or N, which comprises:

(i). reacting a compound of formula (VII) where L represents a leaving group with heterocyclic amine of formula (VIII) where Het is as defined above and all other symbols are as defined above in the presence of a solvent and base at a temperature in the range of −10 to 110° C. to produce a compound of formula (IX) and (ii). oxidizing the compound of formula (IX) using conventional oxidizing agents in the presence of an organic acid to produce a compound a formula (I).

The process is as shown in Scheme-1

Scheme-1

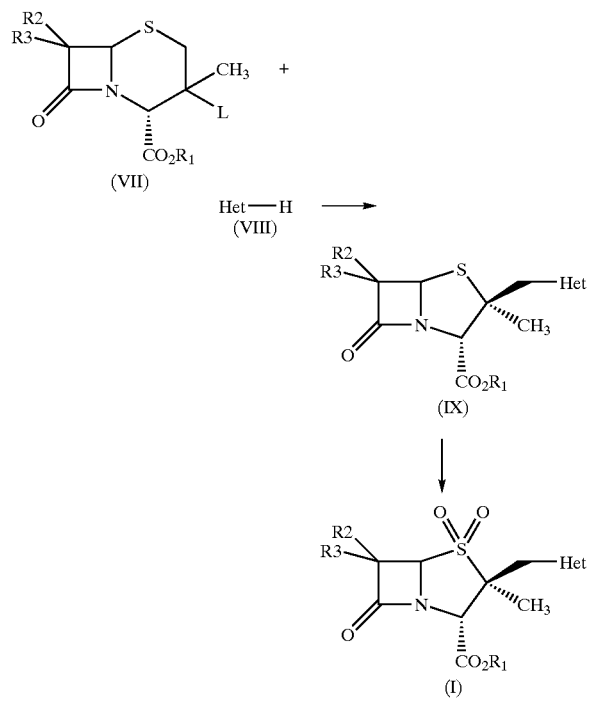

DETAIL DESCRIPTION OF THE INVENTION

In an embodiment of the present invention, the carboxy-protecting group such as ester is selected from p-nitrobenzyl, o-chlorobenzyl, p-methoxyphenyl, diphenylmethyl, and the like.

In another embodiment of the present invention, L represents a leaving group selected from halogen like chloro, bromo, iodo; p-toluenesulphonyloxy, methanesulphonyloxy and the like.

In yet another embodiment of the present invention, the group represented by Het is selected from pyrrolyl, pyrrolidinyl, piperidinyl, imidazolyl, oxazolidinyl, 1,2,3-triazolyl, 1,2,4-triazolyl and the like.

In still another embodiment of the present invention, the group represented by acylamino is selected from phenacetylamino, phenoxyacetylamino, benzoylamino and the like.

In still another embodiment of the present invention, the reaction between the 3-substituted cepham derivative of the formula (VII) and with heterocyclic amine of formula (VIII) is carried out in a suitable solvent in the presence or absence of a phase transfer catalyst in the presence or absence of a base. The molar ratio of the compound of formula (VIII) is about 1 to 30 times, preferably about 1 to 10 times with respect to the cepham compound of the formula (VII). The heterocyclic amine used can either be in free form or as its salt of a mineral acid or an organic sulphonic or carboxylic acid.

The solvents do not play a major role and therefore a wide variety of solvents such as ethereal solvents like THF, dioxane, ethylene glycol dimethylene ether (monoglyme), diethylene glycol dimethylene ether diglyme, etc.; polar aprotic solvents like DMF, DMAc, DMSO, acetone, ethyl acetate, sulpholane, acetonitrile, etc.; protic solvents like n-butanol, isopropanol, methanol, ethanol, cyclohexanol, etc.; aromatic solvents like toluene, anisole, etc.; chlorinated solvents like dichloroethane, dichloromethane, carbon tetrachloride, chlorobenzene, etc.; can be used. These organic solvents can be used as a single solvent or a combination or with some amount of water as an additional component. In the case of water-immiscible solvents, the reaction is conducted in biphasic medium using a phase transfer catalyst under vigorous agitating conditions. The phase transfer catalyst can be a quaternary ammonium salt like tetrabutylammonium bromide, benzyltributylammonium bromide, benzyltrioctylammonium bromide, etc., or a phosphonium salt like benzyltriphenylphosphonium bromide, etc. The base can be inorganic or organic, and preferably an inorganic oxide or a carbonate of alkali or alkaline earth metal like magnesium carbonate, calcium carbonate, cesium carbonate, barium carbonate, potassium hydrogen carbonate, sodium carbonate, sodium hydrogen carbonate, copper oxide, copper carbonate, potassium carbonate, etc. The temperature of the reaction is normally between −10 to 110° C., and preferably between 30 to 65° C.

The product obtained from the above reaction can be either purified to remove the unwanted isomers or taken directly to next step without purification, as the product obtained in the next step takes care of removing impurities and isomers, thereby affording pure compound. The product thus obtained is isolated in paste form and oxidized with an oxidizing agent in aqueous acidic medium. The oxidizing reagent is a conventional sulfur-oxidizer like potassium permanganate, peracetic acid, trifluoroperacetic acid, m-chloroperbenzoic acid, oxone, etc, preferably potassium permanganate. The oxidation can be conducted in the presence of an organic acid like aliphatic carboxylic acid, aliphatic sulphonic acid, etc., preferably acetic acid, methane sulphonic acid, etc. The reaction temperature can vary from −30 to +50° C., and preferably from −10 to +30° C. The time required for the reaction can very from 15 min to 8 hours, preferably 15 min to 2 hours. At the end of the reaction, the reaction mixture is quenched with a suitable reagent to destroy the excess oxidizing reagent and the reaction medium is neutralized with an inorganic base like sodium bicarbonate. At this stage, the product undergoes a purification process in ethyl acetate wherein other isomers of the reaction are getting solubilized in this solvent. The selectivity of purification to remove unwanted isomers of the process is less in other solvents and ethyl acetate is a preferred solvent for getting pure-required-isomer.

In an another embodiment of the present invention, there is provided a process for the preparation of tazobactam derivatives of formula (X) or its salts

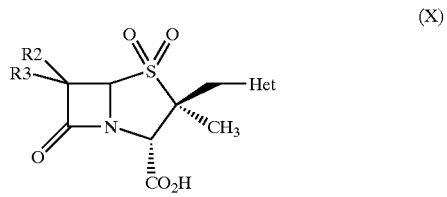

wherein $R_2$ and $R_3$ may be same or different and independently represent hydrogen, halogen, $NH_2$, acylamino, phthalimido with a proviso that both $R_2$ and $R_3$ are not $NH_2$, acylamino, phthalimido; Het represents a 5 or 6 membered nitrogen containing heterocycle ring system having one or more heteroatoms selected from O, S, or N by deesterifying the compound of formula (I).

The deesterification of compound of formula (I) to (X) is carried out by conventional methods. For instance, in the case of the p-nitrobenzyl protecting group, the following methodology illustrates the deprotection to obtain the β-lactam inhibitor of the formula (I). The 2β-triazolylmethyl substituted penam of the formula (I) (n=2; R is a carboxy-protecting group) is converted to the compound of the formula (I) (n=2; R=H) in the presence of a noble metal catalyst, in the presence of an inorganic base in a biphasic medium and a hydrogen source at elevated pressures. The noble metal catalyst can be 5-10% Pd/C, 5% Pt, Adam's catalyst, etc., and preferably 10% Pd/C. The reaction is conducted in the presence or absence of an organic or inorganic base selected from magnesium carbonate, calcium carbonate, cesium carbonate, barium carbonate, potassium hydrogen carbonate, sodium carbonate, sodium hydrogen carbonate, copper oxide, copper carbonate, potassium carbonate and the like. While the reaction can be conducted in a monophasic or biphasic medium, preferably an aqueous-organic biphasic medium is used, comprising of water-immiscible solvent such as toluene, ethyl acetate, methyl acetate, etc., and preferably ethyl acetate. After work up, the product was isolated by crystallization from the aqueous medium.

The process of producing the 2β-triazolylmethylpenam derivative of the formula (I) is described in detail in the reference examples given below which are provided by way of illustration only and should not be considered to limit the scope of the invention.

It is interesting to note that in the five-membered penam derivative obtained from the six-membered cepham derivative, the stereochemical course of the reaction pathway is favorable to produce the β-isomer selectively. In addition, during the ring contraction of the 3-substituted cepham derivatives of the formula (VII) into 2β-heterocyclylmethyl penam derivatives of the formula (I), the configuration of the carboxyl group is unchanged. The carboxyl group is trans to the 2β-triazolylmethyl group. The relative stereochemistry has been confirmed by NOE experiments unequivocally.

EXAMPLE 1

Step (i)

Preparation of 4-nitrobenzyl 2β-(1H-1,2,3-triazol-1-ylmethyl)-2α-methylpenam-3α-carboxyl of the Formula (IX)

To a solution of 4-nitrobenzyl 3-bromo-3-methylcepham-4-carboxylate (50 gm) in acetone (250 mL) contained in a 2 Lit RB flask was added water (65 mL) and 1H-1,2,3-triazole (100 mL) at room temperature. To the clear solution, calcium carbonate (25 gm) was added under vigorous stirring. The reaction mixture was heated to 50–60° C. over a period of 15 min and maintained under vigorous stirring at this temperature for a period of 9 hrs. The progress of the reaction was monitored by TLC. After the reaction was over, the reaction mixture was filtered to remove the inorganic salts and the bed washed with acetone (50 mL). The clear solution was distilled under vacuum to remove acetone at less than 30° C. The solution after removal of acetone was poured in to dichloromethane (250 mL) and stirred well at 26–28° C. The organic layer was separated and washed with purified water (200 mL) four times. The organic layer was concentrated under vacuum to remove dichloromethane, initially at <25° C. and finally at 35–40° C. The paste thus obtained was taken to next step with out purification.

Step (ii)

Preparation of 4-nitrobenzyl 2β-(1H-1,2,3-triazol-1-ylmethyl)-2α-methylpenam-3α-carboxyl of the Formula (I)

To acetic acid (350 mL) at 20° C. in a 2 Lit RB flask, was added 4-nitrobenzyl 2β-(1H-1,2,3-triazol-1-ylmethyl)-2α-methylpenam-3α-carboxylate (as obtained from the above example) and purified water (35 mL). The homogeneous reaction mixture was cooled to 5–10° C. under stirring. To the homogeneous reaction mixture, powdered potassium permanganate (30 gm) was added in 12 lots over a period of 1.5–2.0 hrs while maintaining the temperature at 5–10° C. Stirring was continued for another 0.5 hrs and the reaction was monitored by TLC. After the reaction was over, the reaction mixture was charged into crushed ice (500 gm) under vigorous stirring over a period of 0.5–1.0 hrs. To the mass, cold ethyl acetate (500 mL) was added while maintaining the temperature at 0–5° C. A dilute solution of hydrogen peroxide (25%; 40 mL) was added slowly over a period of 1 hr at such a rate that the temperature was maintained at 0–5° C. After the decolourization was complete, ethyl acetate (200 mL) was added. To the solution, which was almost colorless, sodium chloride (100 gm) was added and stirred well for 15 min. The ethyl acetate layer was separated and washed with water (250 ml) twice. To the ethyl acetate layer, 8% sodium bicarbonate solution (~400 mL) was added slowly until pH of the aqueous layer was >7.2. The reaction mixture was stirred for another 15 min and the pH checked again. After the pH stabilized at >7.2, stirring was stopped and the layers separated. The organic layer was washed with water (250 mL) twice and charcoalized with activated carbon (10 gm). The organic layer was concentrated to remove ethyl acetate under vacuum up to 150 mL when the product separated out from the medium. After maintaining under stirring for 5 hrs, the material was filtered and washed with ethyl acetate (30 mL). Drying under vacuum afforded colorless 4-nitrobenzyl 2β-(1H-1,2,3-triazol-1-ylmethyl)-2α-methylpenam-3α-carboxylate-1,1-dioxide in pure form in 50–75% yield.

Mass m/c: M+1 peak at 436.3; $^1$H NMR data (CDCl$_3$): δ 1.29 (3H, s, 2α-Me), 3.53 (1H, dd, J=1.9 & 16.3 Hz, 7H-trans), 3.61 (1H, dd, J=4.3 & 16.3 Hz, 7H-cis), 4.63 (1H, s, CH—CO$_2$), 4.66 (1H, dd, J=1.9 & 4.2 Hz, 6H), 5.07 (2H, Abq, J=15.1 Hz, 2β-CH$_2$), 5.35 (2H, Abq, J=14 Hz, COO—CH$_2$), 7.61 (2H, d, J=8.7 Hz, aromatic ortho protons), 8.30 (2H, d, J=8.7 Hz, aromatic meta protons), and 7.75 & 7.79 (2H, triazole protons).

Step (iii)

Preparation of 2β-(1H-1,2,3-triazol-1-ylmethyl)-2α-methylpenam-3α-carboxylic acid-1,1-dioxide of the Formula (I)

In to a 2 Lit high-pressure hydrogenator, ethyl acetate (500 mL), 10% Pd/C (2.5 gm), and 4-nitrobenzyl 2β-(1H-1,2,3-triazol-1-ylmethyl)-2α-methylpenam-3α-carboxylate-1,1-dioxide (25 gm) were added. The heterogeneous reaction mixture was cooled to 20–22° C. under stirring. A solution of sodium bicarbonate (24 gm in 375 mL of purified water) was added over 10–15 min at 20–22° C. The hydrogenator was flushed with nitrogen and hydrogen pressure of 200 psi was applied over 10 min at 20–22° C. The hydrogen pressure was maintained for 1.5–2.0 hrs and the progress of the reaction monitored. After the reaction was over, the hydrogen pressure was released and flushed with nitrogen. The reaction mass was cooled to 0–5° C. The catalyst Pd/C was recovered by filtration and the bed washed with chilled purified water (50 mL). The aqueous layer was separated and washed with ethyl acetate (150 mL) three times. The pH was set to 6.4–6.6 with 6N HCl (~37 mL required) and the aqueous layer washed with ethyl acetate (150 mL). The aqueous layer was charcoalized with activated carbon (4 gm) over 15 min and the bed washed with purified water (50 mL). The pH was set to 3.2 with 6N HCl (~60 mL) and maintained for 15 min. Crystallization occurred. Stirring was continued at this pH for 30 min. The pH was further set to 2.5–2.6 with 6N HCl (~15 mL) and maintained for 2 hrs. The crystals were filtered and washed with water followed by ethyl acetate (40 mL). The material was dried under vacuum for 5 hrs at 26–30° C. The yield of the product, 2β-(1H-1,2,3-triazol-1-ylmethyl)-2α-methylpenam-3α-carboxylic acid-1,1-dioxide, was around 85–90%.

Mass m/e: M−1 peak at 299.1; $^1$H NMR data (DMSO-$d_6$): δ 1.33 (3H, s, 2α-Me), 3.31 (1H, dd, J=1.4 & 16.5 Hz, 7H-trans), 3.71 (1H, dd, J=4.5 & 16.5 Hz, 7H-cis), 4.80 (1H, s, CH—$CO_2$), 4.91 (1H, d, J=15.3 Hz, H' of 2β-$CH_2$), 5.19 (1H, dd, J=1.5 & 4.4 Hz, H6), 5.24 (1H, d, J=15.3 Hz, H" of 2β-$CH_2$), and 7.8 & 8.1 (2H, triazole protons). The stereochemistry of the 2α-methyl and 2β-methylene groups was confirmed by NOE experiments.

EXAMPLE 2

Step (i)

Preparation of Diphenylmethyl 2β-(1H-1,2,3-triazol-1-ylmethyl)-2α-methylpenam-3α-carboxylate of the Formula (IX)

To a solution of diphenylmethyl 3-bromo-3-methylcepham-4-carboxylate (200 gm) in acetone (1000 mL) contained in a 2 Lit RB flask was added water (300 mL) and 1H-1,2,3-triazole (400 mL) at room temperature. To the clear solution, calcium carbonate (25 gm) was added under vigorous stirring. The reaction mixture was heated to 50–60° C. over a period of 15 min and maintained under vigorous stirring at this temperature for a period of 6–15 hrs. After the reaction was over, the reaction mixture was filtered to remove the inorganic salts and the bed washed with acetone (50 mL). The clear solution was distilled under vacuum to remove acetone at less than 30° C. The solution, after removal of acetone, was poured into dichloromethane (1200 mL) and stirred well at 26–28° C. The organic layer was separated and washed with purified water five times (5×1 Lit). The organic layer was concentrated under vacuum to remove dichloromethane at <40° C. The paste containing the title compound (~200 gm) thus obtained was taken to next step with out purification.

Step (ii)

Preparation of Diphenylmethyl 2β-(1H-1,2,3-triazol-1-ylmethyl)-2α-methylpenam-3α-carboxylate-1,1-dioxide To acetic acid (900 mL) at 20° C. in a 2 Lit RB flask, was added diphenylmethyl 2β-(1H-1,2,3-triazol-1-ylmethyl)-α-methylpenam-3α-carboxylate (200 gm; as obtained from the above example) and purified water (90 mL). The homogeneous reaction mixture was cooled to 5–10° C. under stirring. To the homogeneous reaction mixture, potassium permanganate (100 gm) was added over 1.5–2.0 hrs at 5–10° C. Stirring was continued for another 2 hrs at 5–10° C. After the reaction was over, the reaction mixture was charged into crushed ice (1000 gm). To the mass, dichloromethane (750 mL) was added at 0–5° C. Hydrogen peroxide (25%; 100 mL) was added at 0–5° C. After the decolourization was complete, dichloromethane (750 mL) was added. The organic layer was separated and the aqueous layer extracted with dichloromethane (1 Lit). The organic layers were combined and washed with water (1 Lit) followed by saturated sodium bicarbonate solution (~400 mL) at pH 6–7. The organic layer was washed with water (1 Lit) and concentrated under vacuum to remove the solvent. The residue was treated with IPE, filtered and washed with IPE and dried under vacuum to afford diphenylmethyl 2β-(1H-1,2,3-triazol-1-ylmethyl)-2α-methylpenam-3α-carboxylate-1,1-dioxide in pure form in 55–75% yield.

Step (iii)

Preparation of 2β-(1H-1,2,3-triazol-1-ylmethyl)-2α-methylpenam-3α-carboxylic acid-1,1-dioxide of the Formula (I)

Into a 2 Lit high-pressure hydrogenator, acetic acid (1000 mL), 10% Pd/C (2.5 gm), and diphenylmethyl 2β-(1H-1,2,3-triazol-1-ylmethyl)-2α-methylpenam-3α-carboxylate-1,1-dioxide (25 gm) were added. The heterogeneous reaction mixture was cooled to 20–22° C. under stirring. The hydrogenator was flushed with nitrogen and a hydrogen pressure of 200 psi was applied over 10 min at 20–22° C. The hydrogen pressure was maintained for 1.5–2.0 hrs and the progress of the reaction monitored. After the reaction was over, the hydrogen pressure was released and flushed with nitrogen. The catalyst Pd/C was recovered by filtration and the bed washed with acetic acid (50 mL). The filtrate was concentrated under vacuum to a residue. The residue was diluted with water and washed with ethyl acetate. The aqueous layer was charcoalized and acidified with 6N HCl to crystallize the title compound. The product was filtered, washed with chilled water followed by ethyl acetate and dried vacuum to afford the pure crystals of 2β-(1H-1,2,3-triazol-1-ylmethyl)-2α-methylpenam-3α-carboxylic acid-1,1-dioxide.

What is claimed is:

1. A process for the preparation of 2β-heterocyclyl methyl penam derivatives of the formula (I),

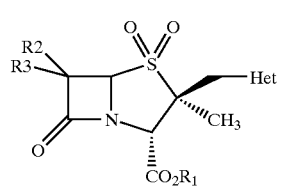

(I)

wherein, $R_1$ carboxylic acid protecting group; $R_2$ and $R_3$ may be same or different and independently represent hydrogen, halogen, $NH_2$, acylamino, phthalimido with provisos that $R_2$ and $R_3$ are not both $NH_2$, $R_2$ and $R_3$ are not both acylamino, and $R_2$ and $R_3$ are not both phthalimido; and wherein Het represents a 5 or 6-membered nitrogen containing a heterocycle ring system having one or more heteroatoms selected from O, S, or N, in which a H is bound to the nitrogen contained in the ring, said process comprising:

(i) reacting a compound of formula (VII)

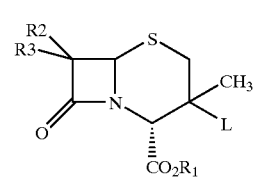

(VII)

wherein, L represents a leaving group and all other substituents are as defined above with heterocyclic amine of formula (VIII)

Het-H                                                                                  (VIII)

wherein, Het is as defined above, in the presence of a solvent and base at a temperature in a range of −10 to 110° C. to produce a compound of formula (IX)

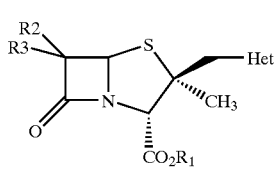

(IX)

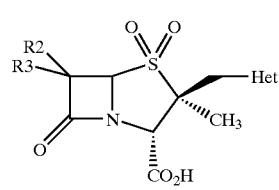

(X)

wherein all substituents are as defined above and (ii) oxidizing the compound of formula (IX) using conventional oxidizing agents in the presence of an organic acid to produce a compound of formula (I).

2. The process according to claim 1, wherein the solvent used in step (i) is selected from a group consisting of THF, dioxane, diglyme, monoglyme, dimethylformamide, dimethylacetamide, dimethylsulfoxide, acetone, ethyl acetate, sulpholane, acetonitrile, n-butanol, isopropanol, methanol, ethanol, cyclohexanol, toluene, anisole, dichloroethane, dichloromethane, carbon tetrachloride, chlorobenzene and or mixtures thereof.

3. The process according to claim 1, wherein the base used in step (i) is selected from a group consisting of magnesium carbonate, calcium carbonate, cesium carbonate, barium carbonate, potassium hydrogen carbonate, sodium carbonate, sodium hydrogen carbonate, copper oxide, copper carbonate and potassium carbonate.

4. The process according to claim 1, wherein the oxidizing agent used in step (ii) is selected from a group consisting of potassium permanganate, peracetic acid, trifluoroperacetic acid, m-chloroperbenzoic acid and oxone.

5. The process according to claim 1, wherein the organic acid used in step (ii) is selected from aliphatic carboxylic acid or aliphatic sulphonic acid.

6. The process according to claim 1, wherein the carboxy protecting group is selected from a group consisting of p-nitrobenzyl, o-chlorobenzyl, p-methoxyphenyl and diphenylmethyl.

7. The process according to claim 1, wherein the leaving group L is selected from a group consisting of chloro, bromo, iodo, p-toluenesulphonyloxy and methanesulphonyloxy.

8. The process according to claim 1, wherein the group represented by Het and is selected from a group consisting of pyrrolyl, pyrrolidinyl, piperidinyl, imidazolyl, oxazolidinyl, 1,2,3-triazolyl or 1,2,4-triazolyl.

9. The process according to claim 1, wherein the acylamino group is selected from phenacetylamino, phenoxyacetylamino or benzoylamino.

10. A process for the preparation of tazobactam derivatives of formula (X) or its salts wherein $R_2$ and $R_3$ may be same or different and independently represent hydrogen, halogen, $NH_2$, acylamino, phthalimido with provisos that $R_2$ and $R_3$ are not both $NH_2$, $R_2$ and $R_3$ are not both acylamino, and $R_2$ and $R_3$ are not both phthalimido; and wherein Het represents a 5 or 6 membered nitrogen containing a heterocycle ring system having one or more heteroatoms selected from O, S and N, in which a H is bound to the nitrogen contained in the ring, said process comprising:

deesterifying the 2β-heterocycle methyl penam derivative of the formula (I), which is obtained by a process as claimed in claim 1.

11. The process according to claim 10, wherein the group represented by Het and is selected from a group consisting of pyrrolyl, pyrrolidinyl, piperidinyl imidazolyl, oxazolidinyl, 1,2,3-triazolyl or 1,2,4-triazolyl.

12. The process according to claim 10, wherein the Het group is 1,2,3-triazolyl.

13. The process according to claim 1, wherein the temperature is in a range between 30 to 65° C.

14. The process according to claim 1, wherein the reacting step (i) is carried out in the presence of a phase transfer catalyst.

15. The process according to claim 14, wherein the phase transfer catalyst is selected from the group consisting of tetrabutylammonium bromide, benzyltributylammonium bromide, benzyltrioctylammonium bromide, and benzyltriphenylphosphonium bromide.

16. The process according to claim 1, wherein the reacting step (i) is carried out in the absence of a phase transfer catalyst.

17. The process according to claim 1, wherein a molar amount of the heterocyclic amine of formula (VIII) is about 1 to 30 times a molar amount of the compound of formula (VII) in the reacting step (i).

18. The process according to claim 1, wherein a molar amount of the heterocyclic amine of formula (VIII) is about 1 to 10 times a molar amount of the compound of formula (VII) in the reacting step (i).

19. The process according to claim 1, wherein the carboxyl group does not change configuration during contraction of the compound of formula (VII) into 2β-heterocyclyl methyl penam derivative of the formula (I).

20. The process according to claim 1, wherein the carboxyl group is trans to the Het during contraction of the compound of formula (VII) into 2β-heterocyclyl methyl penam derivatives of the formula (I).

* * * * *